(12) United States Patent
Pirkl et al.

(10) Patent No.: US 8,835,591 B2
(45) Date of Patent: Sep. 16, 2014

(54) METHOD FOR PREPARING POLYURETHANE PREPOLYMERS CONTAINING ISOCYANATE GROUPS

(75) Inventors: Hans-Georg Pirkl, Leverkusen (DE); Manfred Schmidt, Dormagen (DE); Robert Vieler, Dormagen (DE); Ursula Tracht, Leverkusen (DE); Peter Weuta, Leverkusen (DE); Sigurd Buchholz, Köln (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/809,639

(22) PCT Filed: Jul. 11, 2011

(86) PCT No.: PCT/EP2011/061739
§ 371 (c)(1),
(2), (4) Date: Mar. 1, 2013

(87) PCT Pub. No.: WO2012/007419
PCT Pub. Date: Jan. 19, 2012

(65) Prior Publication Data
US 2013/0158291 A1 Jun. 20, 2013

(30) Foreign Application Priority Data

Jul. 13, 2010 (DE) .......... 10 2010 027 052

(51) Int. Cl.
*C08G 77/00* (2006.01)
*C07C 263/16* (2006.01)
*B29B 7/76* (2006.01)
*C08G 18/10* (2006.01)
*C08G 18/08* (2006.01)

(52) U.S. Cl.
CPC ............. *C07C 263/16* (2013.01); *B29B 7/7663* (2013.01); *C08G 18/10* (2013.01); *C08G 18/0895* (2013.01)
USPC ............................................................ 528/49

(58) Field of Classification Search
CPC ..................... C08G 18/10; C08G 18/00–18/06
See application file for complete search history.

(56) References Cited

U.S. PATENT DOCUMENTS

| 3,267,050 A | 8/1966 | Kuryla et al. |
| 3,304,273 A | 2/1967 | Stamberger |
| 3,383,351 A | 5/1968 | Stamberger |

(Continued)

FOREIGN PATENT DOCUMENTS

| CA | 2272812 A1 | 11/1999 |
| DE | 1111394 B | 7/1961 |

(Continued)

OTHER PUBLICATIONS

International Search Report for PCT/EP2011/061739 mailed Oct. 17, 2011.

*Primary Examiner* — Karl J Puttlitz
(74) *Attorney, Agent, or Firm* — Drinker Biddle & Reath LLP

(57) ABSTRACT

The present invention relates to the technical field of isocyanates. The present invention provides a method for preparing NCO prepolymers by reacting a stoichiometric excess of an organic isocyanate with an isocyanate-reactive component, the reaction components being mixed together and the mixture being introduced directly into a storage or transport vessel, where it reacts to completion.

8 Claims, 2 Drawing Sheets

(56) References Cited

U.S. PATENT DOCUMENTS

| | | | |
|---|---|---|---|
| 3,523,093 A | 8/1970 | Stamberger | |
| 4,061,313 A | 12/1977 | Brauner et al. | |
| 4,304,708 A | 12/1981 | Marx et al. | |
| 4,374,209 A | 2/1983 | Rowlands | |
| 5,278,274 A * | 1/1994 | Verhelst et al. | 528/44 |
| 6,495,652 B1 * | 12/2002 | Reichelt et al. | 528/59 |

FOREIGN PATENT DOCUMENTS

| | | |
|---|---|---|
| DE | 1152536 B | 8/1963 |
| DE | 1152537 B | 8/1963 |
| DE | 1215373 B | 4/1966 |
| DE | 1222669 B | 8/1966 |
| DE | 2532355 A1 | 1/1977 |
| DE | 2823762 A1 | 12/1978 |
| DE | 3231497 A1 | 3/1984 |
| DE | 19823392 A1 | 12/1999 |
| DE | 19823393 A1 | 12/1999 |
| DE | 69132613 T2 | 10/2001 |
| EP | 011752 A1 | 6/1980 |
| EP | 0480588 A2 | 4/1992 |
| EP | 0722962 A2 | 7/1996 |
| GB | 969965 A | 9/1964 |
| GB | 987618 A | 3/1965 |
| GB | 1033912 A | 6/1966 |
| GB | 1040452 A | 8/1966 |
| WO | WO-94/29361 A1 | 12/1994 |
| WO | WO-01/91897 A1 | 12/2001 |

* cited by examiner

METHOD FOR PREPARING POLYURETHANE PREPOLYMERS CONTAINING ISOCYANATE GROUPS

RELATED APPLICATIONS

This application is a national stage application (under 35 U.S.C. §371) of PCT/EP2011/061739, filed Jul. 11, 2011, which claims benefit of German application 10 2010 027 052.0, filed Jul. 13, 2010.

The present invention relates to the technical field of isocyanates. The present invention provides a method for preparing NCO prepolymers by reacting a stoichiometric excess of an organic isocyanate with an isocyanate-reactive component, the reaction components being mixed together and the mixture being introduced directly into a storage or transport vessel, where it reacts to completion.

Isocyanate group-containing polyurethane prepolymers, which can be obtained by reacting a stoichiometric excess of an organic polyisocyanate with an organic polyol, are known in the field of polyurethanes. They have a free isocyanate content of 2 to 15 wt. % and are used for example in the production of elastomers, coatings, adhesives and the like.

The preparation of such NCO prepolymers has been described in numerous publications.

DE69132613T2 describes how the reaction between a polyol and a polyisocyanate proceeds exothermically. In order to achieve a complete reaction within an acceptable time, the reaction mixture would normally be heated to a temperature in the range from approximately 40 to approximately 100° C. for an hour or more.

WO94/29361A1 describes the preparation of prepolymers having NCO contents of 5 to 10 wt. % by reacting isocyanates with polyols in a temperature range from 40 to 80° C., the reaction being performed in the conventional manner, i.e. in an appropriate reaction vessel.

According to DE2823762A1 the reaction between diisocyanates and polyhydroxyl compounds to synthesise thermoplastic polyurethanes takes place by directing the starting components through a mixing zone and then through a reaction zone.

According to the description in DE2823762A1 the reaction components remain in the reaction zone until the polyaddition is complete.

DE19823392A1 describes a reaction of isocyanate with polyol in the process stream of the isocyanate-producing plant at temperatures of 40 to 100° C. In EP0722962A2 a foaming plant is used, and in particular its mixing head, both to prepare prepolymers and then to foam them.

The methods for preparing NCO prepolymers that are described in the prior art require a reaction of an isocyanate group-containing component with an isocyanate group-reactive component in a reactor, in particular under controlled mixing and temperature conditions.

Starting from the prior art a person skilled in the art sets out to provide a flexible method for preparing NCO prepolymers by means of which NCO prepolymers can be produced easily and quickly. It would be desirable for the preparation of NCO prepolymers to be possible even if no production plants are available. It would furthermore be desirable for the production of different NCO prepolymers to be possible without any great effort being involved, in terms of cleaning reactors for example.

Surprisingly it has been found that an isocyanate group-containing component in a hyperstoichiometric amount and an isocyanate group-reactive component in a hypostoichiometric amount can be continuously brought together in a mixing device at room temperature and the reactive mixture introduced directly into a storage or transport vessel, where the components react reproducibly to form an isocyanate group-containing prepolymer with no further mixing and with no temperature control.

The present invention therefore firstly provides a method for preparing an isocyanate group-containing prepolymer from an isocyanate group-containing component and an isocyanate group-reactive component, characterised in that the components are continuously mixed in a mixing device and immediately after being mixed the reaction mixture is introduced continuously into a storage or transport vessel, where the reaction between the components is completed.

Unlike the methods described in the prior art, the reaction of an isocyanate group-containing component and an isocyanate group-reactive component does not take place in a conventional reaction vessel; instead the components are continuously brought together in a mixing device and the reacting mixture is introduced directly into a storage vessel or transport vessel. In this respect the present invention also provides a method for introducing a reacting mixture comprising an isocyanate group-containing component and an isocyanate group-reactive component into a storage or transport vessel, the method of introduction comprising the same features as the method according to the invention for preparing an isocyanate group-containing prepolymer. Therefore no distinction is made below between the method of introduction and the method of preparation. If the method of introduction or the method of preparation is described in more detail, the description is always deemed to refer to both methods.

The general term vessel is also used below for the terms storage vessel and transport vessel.

The bringing together of the components and the introduction of the reactive mixture into the vessel conventionally take place continuously until the vessel is full. Then the process of bringing together and introduction is generally stopped and optionally continued at a later time when a vessel that is not yet full is available. In this respect the processes of bringing together the components and introducing the reactive mixture are performed continuously in batches.

The reaction between the components takes place predominantly in the vessel. This means that the residence time in the mixing device serves substantially only to mix the components. The vessel provides a chamber in which the components can react with each other and form the desired product.

Figure 1:
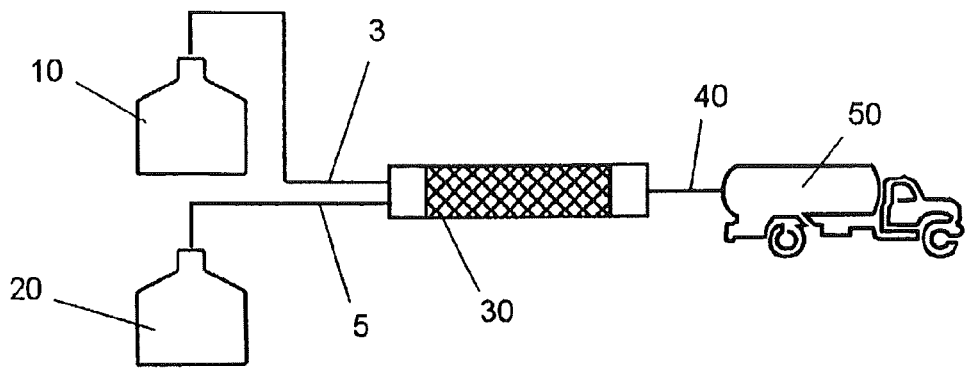
FIG. 1 shows a schematic view of the concept according to the invention.

In a preferred embodiment of the present invention the reaction chamber provided by the vessel is transportable, i.e. it serves to transport the product to its place of destination. The method according to the invention thus has the advantage that no production capacities have to be provided for the preparation of isocyanate group-containing prepolymers. The reaction components can be transferred as required from storage tanks directly into a transport vessel via a mixing device. The invention thus allows a batchwise operation for the rapid filling of individual product containers with no additional reaction chambers or buffer tanks. The reaction of the reaction components to form the desired product can be completed whilst the transport vessel is already on the way to the place of destination.

A transport vessel is understood here to be a vessel that conventionally serves to transport chemicals, in particular isocyanates. The vessel is designed to be transportable, in other words it can be moved to another location by suitable means of transportation.

In particular, a transport vessel is characterised in that it generally has no means of mixing and/or no means of temperature control. Such means, such as in particular means of cooling, can be dispensed with in the method according to the invention.

In a further preferred embodiment the vessel is a storage vessel in which the reaction product can be stored.

The reaction components are preferably brought together in such a way that the rise in temperature in the vessel used is less than 60° C.; the rise in temperature is preferably less than 40° C., particularly preferably less than 20° C., still more preferably less than 10° C. and most preferably a maximum of 5° C. A slight rise in temperature is preferred as the vessel includes no means of cooling, and so for safety reasons the rise in temperature must be restricted. A rise in temperature can additionally exert a negative influence on the product quality.

The aforementioned maximum rise in temperature is preferably established by the mixing ratio of the reaction components.

In the method according to the invention an isocyanate group-containing component in a hyperstoichiometric amount and an isocyanate group-reactive component in a hypostoichiometric amount are reacted together. The proportion of isocyanate group-reactive component in the mixture is preferably 0.1 to 10 wt. %, particularly preferably 0.5 to 8 wt. %, most particularly preferably 1 to 5 wt. %.

Using the present invention new products can be produced easily and quickly without cleaning reactors by varying the mixing ratio of the components and/or the feedstocks such that different prepolymers having a variable isocyanate content are obtained.

The reaction components, i.e. the isocyanate group-containing and the isocyanate group-reactive component, are brought together by means of a mixing device before the reacting mixture enters the vessel. The components are brought together from separate receivers by means of suitable conveying devices such as pumps for example. The sum of the volumetric flow rates of the components during the introduction of the reactive mixture into a tanker vehicle with a capacity of 20,000 liters and a tolerated filling time of 60 minutes is approximately 5.6 liters/second, for example.

The required residence time in the mixing device is dependent on the mixing action of the mixing device. The purpose of mixing is to achieve a "homogeneous" distribution of the components in the reacting mixture. Within the meaning of the present invention a "homogeneous" distribution is achieved when a further mixing action exerted on the distribution leads to no perceptible change in the resulting product in terms of its chemical and physical properties.

Surprisingly it has been found that mixing times of a few seconds are adequate.

The mixing device has one or more static and/or dynamic mixers. Suitable dynamic mixers are for example rotor-stator homogenisers (such as the Megatron FM10/50/2 from Kinematica, Switzerland) or comparable instruments.

Static mixers are preferably used. Whilst in dynamic mixers the homogenisation of a mixture is achieved by means of moving elements, in static mixers the flow energy of the fluid is used: a conveying unit (for example a pump) pushes the fluid through a pipe provided with built-in static mixing equipment, wherein the fluid following the main axis of flow is divided into split streams which, depending on the type of built-in equipment, are expanded, sheared, vortexed together and mixed together.

A review of various types of static mixers can be found in the article "Statische Mischer und ihre Anwendungen", M. H. Pahl and E. Muschelknautz, Chem.-Ing. Techn. 52 (1980) No. 4, p. 285-291.

Static mixers that can be used according to the invention are also described for example in Chem.-Ing. Techn. 52, No. 4, page 285 to 291 and in "Mischen von Kunststoff und Kautschukprodukten", VDI-Verlag, Düsseldorf 1993. Mixers having crossbars are preferably used, as described in DE2532355A1. SMX static mixers from Sulzer are mentioned by way of example. The use of microstructured static mixers such as those sold by Ehrfeld Mikrotechnik BTS GmbH for example is also conceivable; however they have a tendency to block.

Rinsing cycles with one component in conjunction with a suitable valve for the inflow of the other component are critical for preventing blockages before, after and/or in the mixing device during stoppages between two filling operations.

In a preferred embodiment only a first reaction component, preferably the isocyanate group-containing component, is initially directed through the mixing device into the vessel in a first step. These first runnings are a constituent of the product. In a second step, in addition to the first reaction component, the second reaction component, preferably the isocyanate group-reactive component, is likewise directed into the mixing device, where it is mixed with the first reaction component. In other words during the second step both the first and the second reaction component are directed into the mixing device. The mixture passes directly into the vessel. To end the batch production, in a third step the metering of the second reaction component is stopped and the mixing device is rinsed with the first reaction component. Particular importance is attached to the rinsing of the metering unit for the second reaction component: the part of the inflow for the second reaction component located directly ahead of the mixing device is rinsed firstly with an inert substance, preferably nitrogen or a noble gas, and only then with the first reaction component, by means of a three-way tap for example. Then the mixing device remains in the flooded state (flooded with the first reaction component) at ambient temperature until the start of the next batch production.

The aliphatic, cycloaliphatic, araliphatic and aromatic polyvalent isocyanates known per se are suitable for example as the isocyanate group-containing component for the method according to the invention.

The following isocyanates are mentioned by way of example: alkylene diisocyanates having 4 to 12 carbon atoms in the alkylene radical, such as 1,12-dodecane diisocyanate, 2-ethyl tetramethylene diisocyanate-1,4,2-methyl pentamethylene diisocyanate-1,5, tetramethylene diisocyanate-1,4 and preferably hexamethylene diisocyanate-1,6, cycloaliphatic diisocyanates, such as cyclohexane-1,3- and -1,4-diisocyanate and any mixtures of these isomers, 1-isocyanato-3,3,5-trimethyl-5-isocyanatomethyl cyclohexane (IPDI), 2,4- and 2,6-hexahydrotoluoylene diisocyanate and the corresponding mixtures of isomers, 4,4'-, 2,2'- and 2,4'-dicyclohexylmethane diisocyanate and the corresponding mixtures of isomers, and preferably aromatic di- and polyisocyanates, such as for example 2,4- and 2,6-TDI and the corresponding mixtures of isomers, 4,4'-, 2,4'- and 2,2'-MDI and the corresponding mixtures of isomers, mixtures of 4,4'- and 2,2'-MDI, polyphenyl polymethylene polyisocyanates, mixtures of 4,4'-, 2,4'- and 2,2'-MDI and polyphenyl polymethylene polyisocyanates (crude MDI) and mixtures of crude MDI and TDI. The organic di- and polyisocyanates can be used individually or in the form of any mixtures.

Compounds or mixtures of compounds having one or more acidic hydrogen atoms are suitable as isocyanate group-reactive components.

Compounds having a functionality of 2 to 4, preferably 2 to 3, and a molecular weight of 300 to 8000, preferably 300 to 5000, are conveniently used as compounds having at least two acidic hydrogen atoms. Polyether polyamines and/or preferably polyols selected from the group of polyether polyols, polyester polyols, polythioether polyols, polyester amides, hydroxyl group-containing polyacetals and hydroxyl group-containing aliphatic polycarbonates or mixtures of at least two of the cited polyols, for example, have proved themselves. Polyester polyols and/or polyether polyols are preferably used. As a rule the hydroxyl value of the polyhydroxyl compounds is 20 to 80 and preferably 28 to 56 mg KOH/g.

Suitable polyester polyols can be prepared for example from organic dicarboxylic acids having 2 to 12 carbon atoms, preferably aliphatic dicarboxylic acids having 4 to 6 carbon atoms, and polyhydric alcohols, preferably diols, having 2 to 12, preferably 2 to 6 carbon atoms. Suitable dicarboxylic acids are, for example: succinic acid, glutaric acid, adipic acid, suberic acid, azelaic acid, sebacic acid, decane dicarboxylic acid, maleic acid, fumaric acid, phthalic acid, isophthalic acid and terephthalic acid. The dicarboxylic acids can be used both individually and mixed with one another. In place of the free dicarboxylic acids, the corresponding dicarboxylic acid derivatives, such as for example dicarboxylic acid esters of alcohols having 1 to 4 carbon atoms or dicarboxylic anhydrides, can also be used. Dicarboxylic acid mixtures comprising succinic, glutaric and adipic acid, in ratios of for example 20 to 35:35 to 50:20 to 32 parts by weight, and in particular adipic acid, are preferably used. Examples of dihydric and polyhydric alcohols, in particular diols, are: ethanediol, diethylene glycol, 1,2- and 1,3-propanediol, dipropylene glycol, 1,4-butanediol, 1,5-pentanediol, 1,6-hexanediol, 1,10-decanediol, glycerol and trimethylolpropane. Ethanediol, diethylene glycol, 1,4-butanediol, 1,5-pentanediol and 1,6-hexanediol are preferably used. Polyester polyols of lactones, for example ε-caprolactone or hydroxycarboxylic acids, for example ω-hydroxycaproic acid, can also be used.

To prepare the polyester polyols, the organic, for example aromatic and preferably aliphatic, polycarboxylic acids and/or derivatives and polyhydric alcohols can be polycondensed without catalyst or preferably in the presence of esterification catalysts, conveniently in an atmosphere of inert gas, such as for example inter alia nitrogen, carbon monoxide, helium, argon, in the melt at temperatures of 150 to 250° C., preferably 180 to 220° C., optionally under reduced pressure, up to the desired acid value, which is advantageously less than 10, preferably less than 2. According to a preferred embodiment, the esterification mixture is polycondensed at the aforementioned temperatures until an acid value of 80 to 30, preferably 40 to 30 mg KOH/g is obtained, under normal pressure and then under a pressure of less than 500 mbar, preferably 50 to 150 mbar. Suitable esterification catalysts include, for example, iron, cadmium, cobalt, lead, zinc, antimony, magnesium, titanium and tin catalysts in the form of metals, metal oxides or metal salts. The polycondensation can also take place in the liquid phase, however, in the presence of diluents and/or entraining agents, such as for example benzene, toluene, xylene or chlorobenzene, to distil off the condensation water azeotropically.

To prepare the polyester polyols the organic polycarboxylic acids and/or derivatives and polyhydric alcohols are advantageously polycondensed in the molar ratio of 1:1 to 1:8, preferably 1:1.05 to 1.2.

The polyester polyols obtained preferably have a functionality of 2 to 4, in particular 2 to 3, and a molecular weight of 480 to 3000, in particular 600 to 2000.

However, polyether polyols prepared by known methods, for example by anionic polymerisation with alkali hydroxides such as for example sodium or potassium hydroxide or alkali alcoholates such as for example sodium methylate, sodium or potassium ethylate or potassium isopropylate as catalysts and with the addition of at least one starter molecule containing 2 to 4, preferably 2 to 3 reactive hydrogen atoms in bonded form, or by cationic polymerisation with Lewis acids such as inter alia antimony pentachloride, boron fluoride etherate or bleaching earth as catalysts, from one or more alkylene oxides having 2 to 4 carbon atoms in the alkylene radical, are used in particular as polyols.

Suitable alkylene oxides are for example tetrahydrofuran, 1,3-propylene oxide, 1,2- and 2,3-butylene oxide, styrene oxide and preferably ethylene oxide and 1,2-propylene oxide. Suitable starter molecules are, for example: water, organic dicarboxylic acids, such as succinic acid, adipic acid, phthalic acid and terephthalic acid, aliphatic and aromatic, optionally N-mono-, N,N- and N,N'-dialkyl-substituted diamines having 1 to 4 carbon atoms in the alkyl radical, such as optionally mono- and dialkyl-substituted ethylene diamine, diethylene triamine, triethylene tetramine, 1,3-propylene diamine, 1,3- and 1,4-butylene diamine, 1,2-, 1,3-, 1,4-, 1,5- and 1,6-hexamethylene diamine, phenylene diamine, 2,3-, 2,4- and 2,6-toluoylene diamine, and 4,4'-, 2,4'- and 2,2'-diaminodiphenylmethane. Also suitable as starter molecules are: alkanol amines, such as for example ethanolamine, N-methyl- and N-ethyl ethanolamine, dialkanol amines, such as for example diethanolamine, N-methyl- and N-ethyl diethanolamine, and trialkanol amines, such as for example triethanolamine, and ammonia. Polyhydric, in particular dihydric and/or trihydric alcohols, such as ethanediol, propanediol-1,2 and -2,3, diethylene glycol, dipropylene glycol, butanediol-1,4, hexanediol-1,6, glycerol, trimethylolpropane and pentaerythritol are preferably used, whilst predominantly higher-functional starters such as for example sorbitol and sucrose are used for rigid foam polyetherols.

The polyether polyols, preferably polyoxypropylene and polyoxypropylene polyoxyethylene polyols, have a functionality of preferably 2 to 4 and in particular 2 to 3 and molecular weights of 300 to 8000, preferably 300 to 6000 and in particular 1000 to 5000, and suitable polyoxytetramethylene glycols have a molecular weight of up to approximately 3500, whilst in rigid foam polyetherols molecular weights of 300 to 1000 are the rule.

Also suitable as polyether polyols are polymer-modified polyether polyols, preferably graft polyether polyols, in particular those based on styrene and/or acrylonitrile, which are prepared by in-situ polymerisation of acrylonitrile, styrene or preferably mixtures of styrene and acrylonitrile, for example in the weight ratio 90:10 to 10:90, preferably 70:30 to 30:70, conveniently in the aforementioned polyether polyols in an analogous manner to the details given in DE 11 11 394, DE 12 22 669 (U.S. Pat. No. 3,304,273, U.S. Pat. No. 3,383,351, U.S. Pat. No. 3,523,093), DE 11 52 536 (GB 1040452) and DE 11 52 537 (GB 987618), and polyether polyol dispersions which contain for example as the disperse phase, conventionally in an amount from 1 to 50 wt. %, preferably 2 to 25 wt. %: polyureas, polyhydrazides, polyurethanes containing tertiary amino groups in bonded form and/or melamine and which are described for example in EP-B-011 752 (U.S. Pat. No. 4,304,708), U.S. Pat. No. 4,374,209 and DE-A-32 31 497.

Just like the polyester polyols, the polyether polyols can be used individually or in the form of mixtures. They can moreover be mixed with the graft polyether polyols or polyester polyols and the hydroxyl group-containing polyester amides, polyacetals, polycarbonates and/or polyether polyamines.

Suitable hydroxyl group-containing polyacetals are for example the compounds that can be prepared from glycols, such as diethylene glycol, triethylene glycol, 4,4'-dihydroxyethoxy diphenyl dimethylmethane, hexanediol and formaldehyde. Suitable polyacetals can also be prepared by polymerisation of cyclic acetals.

Suitable polycarbonates containing hydroxyl groups are those of the type known per se, which can be prepared for example by reacting diols, such as propanediol-1,3, butanediol-1,4 and/or hexanediol-1,6, diethylene glycol, triethylene glycol or tetraethylene glycol with diaryl carbonates, for example diphenyl carbonate, or phosgene.

The polyester amides include for example those obtained from polyvalent, saturated and/or unsaturated carboxylic acids or anhydrides thereof and polyhydric saturated and/or unsaturated amino alcohols or mixtures of polyhydric alcohols and amino alcohols and/or polyamines, predominantly linear condensates.

Suitable polyether polyamines can be prepared from the aforementioned polyether polyols by known methods. The cyanoalkylation of polyoxyalkylene polyols and subsequent hydrogenation of the nitrile formed (U.S. Pat. No. 3,267,050) or the partial or complete amination of polyoxyalkylene polyols with amines or ammonia in the presence of hydrogen and catalysts (DE 12 15 373) are mentioned by way of example.

The solvents, auxiliary substances and/or additives and/or catalysts known to the person skilled in the art and seeming to be suitable can moreover be added to the isocyanate group-containing component and/or the isocyanate group-reactive component (see for example DE 198 23 392 A1).

The weakly modified isocyanates prepared according to the invention are suitable inter alia for preparing polyurethane foams.

The invention is illustrated in more detail below by reference to examples, without however being limited thereto.

FIG. 1 shows a schematic view of the concept according to the invention for introducing a reacting mixture comprising an isocyanate group-containing and an isocyanate group-reactive component into a transport vessel. The components are taken from separate receivers (10, 20) through feed inlets (3, 5) into a mixing chamber 30, in which the components are homogeneously mixed. The mixture passes through an outlet 40 into the tank 50 of a tanker vehicle.

Figure 2A:
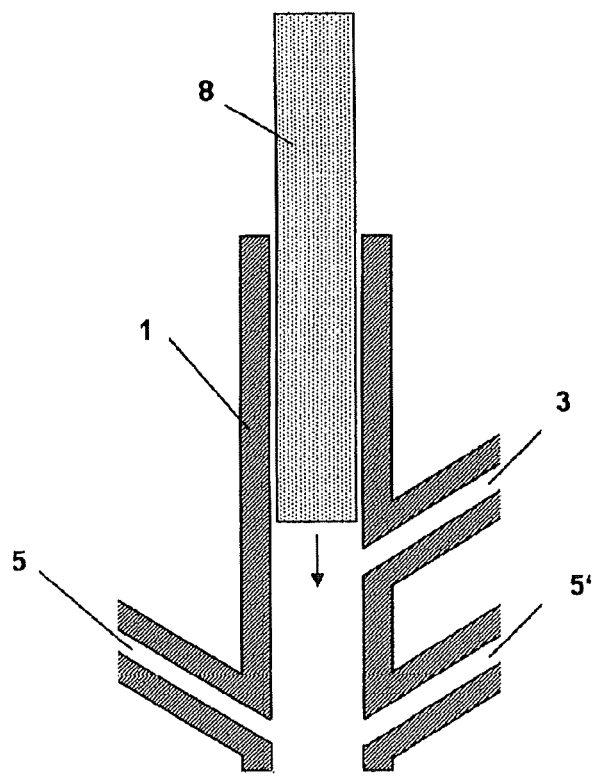
FIGS. 2a and 2b show a schematic view of the device for introducing a reacting mixture into a vessel.
Figure 2B:
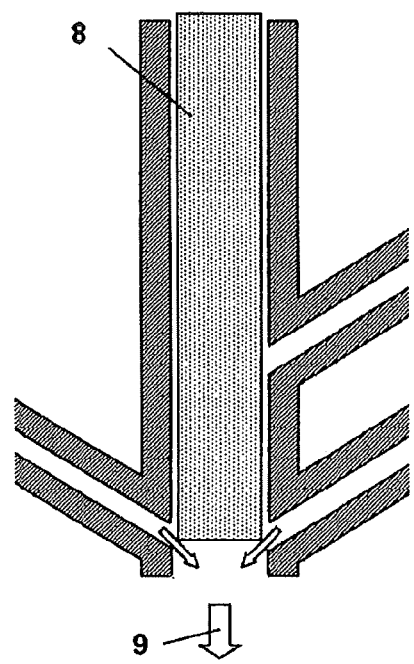

FIGS. 2(a) and 2(b) show schematic views of part of a device for introducing a reacting mixture into a vessel. The illustrated part comprises a pipe 1 incorporating a piston 8. Reacting substances can be introduced into the pipe via feed inlets 3, 5, 5'. One component is introduced via feed inlet 3 and the other component via feed inlets 5 and 5'. The piston 8 is designed to be able to move within the pipe 1.

The device is suitable in particular for bringing together an isocyanate group-containing component and an isocyanate group-reactive component. One of the components (K2) is introduced via feed inlet 3; the other component (K1) via feed inlets 5 and 5'. At the end of feeding the piston 8 is moved down. In doing so it closes off feed inlet 3, so that no more component K2 enters the pipe. As it moves down it pushes residues of component K2 out of the pipe 1 towards the mixing chamber (the direction towards the mixing chamber is indicated by the arrow 9). The feed inlets 5 and 5' are mounted in such a way that they rinse the lower end of the piston 8 with component K1, such that no more residues of K2 remain in the pipe. The feed inlets for components K1 are preferably arranged radially in the pipe 1 facing the piston 8. FIGS. 2(a) and 2(b) show in cross-section two feed inlets for component K1 (5,5'). In a preferred embodiment n feed inlets for component K1 are arranged radially, n being a whole number in the range from 3 to 20, preferably in the range from 3 to 10, most preferably in the range from 4 to 8.

The device illustrated in FIGS. 2(a) and 2(b) is designed in such a way that during the filling according to the invention of a vessel no residues/strands of unincorporated component K2 remain in the device. Residues of this unreacted or unincorporated bulk phase would otherwise continue to react in the device and possibly lead to the formation of blockages.

REFERENCE NUMERALS

1 Pipe
3 Feed inlet
5 Feed inlet
5' Feed inlet
8 Piston
9 Towards mixing chamber
10 Receiver
20 Receiver
30 Mixing chamber
40 Outlet
50 Transport vessel

EXAMPLES

Continuous Reaction of a Polyol Component with an Isocyanate Component

A polyol component and an isocyanate component were brought together in a device as shown schematically in FIGS. 2(a), (b).

The polyol component was pre-heated to the desired temperature by circulating it through an oil-heated heat exchanger by means of a gear pump and by heating the receiver (10). The possibility of being heated likewise existed for the isocyanate component, or alternatively it was metered in at ambient temperature. Both reactants were fed to a mixing module (30) by gear pumps.

An SMX static mixer from Sulzer, Switzerland, served as the mixing module in one case, a Megatron FM 10-50/2 dynamic mixer from Kinematica, Switzerland, in the other case. However, the mixing module used had no perceptible influence on the product quality.

The exact metering flows of both reactants were recorded by mass flowmeters and used to control the rate of flow.

To start a batch production pure MDI was first directed through the plant for a short time. These first runnings were a constituent of the product and were collected in the product vessel. The main run began with the start of polyol metering. The desired composition of the reacting mixture was ensured by increasing the polyol metering during the main run accordingly so that the total amounts of both components metered in corresponded to the target isocyanate:polyol ratio. The last isocyanate runnings occurring during shutdown were likewise taken into account. The amounts of first runnings and last runnings were small when compared with the amount of mixture produced during the main run. To end the batch production the metering of the polyol component was stopped and the plant was rinsed with pure isocyanate.

Then the plant remained in the flooded state at ambient temperature until the start of the next batch production. This procedure had the added advantage that no waste products are formed.

Table 1 summarises various process runs and their results. All reactants are commercially available from Bayer MaterialScience AG.

Descriptions:

MDI 44V20L: Desmodur® 44 V 20 L, mixture of 4,4'-diphenylmethane diisocyanate (MDI) and higher-functional homologues (pMDI) with a viscosity at 25° C. of ≥160 mPas to ≤240 mPas; Bayer MaterialScience AG. The product contains approx. 45% binuclear MDI.

PEP 53D: Polyester polyol based on adipic acid, phthalic acid and diethylene glycol with an OH value of approx. 210 mg (KOH)/g and a viscosity of 10.4 Pa s at 20° C.; Bayer MaterialScience AG.

P293: Bifunctional polyester ether polyol, EO adduct of a mixture of phthalic anhydride, diethylene glycol and ethylene diamine with an OH value of 275 to 325 mg (KOH)/g and a viscosity of 6.5+/−1.3 Pa s at 25° C.; Bayer MaterialScience AG.

DEG: Diethylene glycol, OH value 1055 mg (KOH)/g, viscosity 38 mPa s at 20° C.

TABLE 1

| Isocyanate component | Polyol component | Percentage by weight of polyol, integral | Mass flow of isocyanate [kg/h] | Mass flow of polyol [kg/h] | First + last runnings [%] | Temperature of isocyanate [° C.] | Temperature of polyol [° C.] | Viscosity [mPas] | NCO content [%] |
|---|---|---|---|---|---|---|---|---|---|
| MDI 44V20L | PEP 53D | 5.0 | 427 | 23 | 0 | 40 | 40 | 590 | 28.8 |
| MDI 44V20L | P293 | 4.0 | 384 | 16 | 0 | 40 | 40 | 724 | 29.0 |
| MDI 44V20L | P293 | 4.0 | 384 | 17.7 | 33 | 40 | 40 | 729 | 29.0 |
| MDI 44V20L | P293 | 3.5 | 386 | 14.5 | 4.3 | 40 | 40 | 635 | 29.0 |
| MDI 44V20L | P293 | 3.5 | 386 | 14.5 | 4.3 | 40 | 40 | 540 | 29.3 |
| MDI 44V20L | P293 | 3.5 | 347.4 | 12.6 | 0 | 17 | 40 | 550 | 29.4 |
| MDI 44V20L | DEG | 1.5 | 394 | 6 | 0 | 40 | 20 | 660 | 29.2 |

The invention claimed is:

1. A method for preparing an isocyanate group-containing prepolymer from an isocyanate group-containing component and an isocyanate group-reactive component, which comprises mixing continuously the components in a mixing device and immediately after being mixed introducing continuously the reaction mixture into a storage or transport vessel, where the reaction between the components is completed, wherein in a first step of a batch production only a first reaction component is initially directed through the mixing device into the vessel, before in a second step the second reaction component is directed into the mixing device in addition to the first reaction component, where it is mixed with the first reaction component, wherein to end the batch production the metering of the second reaction component is stopped and the mixing device is rinsed with the first reaction component, and wherein the reaction component directed through the mixing device in the first step of the batch production is the isocyanate group-containing component and the reaction component directed into the mixing device in the second step is the isocyanate group-reactive component.

2. The method according to claim 1, wherein the storage or transport vessel has no means of mixing and/or cooling.

3. The method according to claim 1, wherein the transport vessel is the tank of a tanker vehicle.

4. The method according to claim 1, wherein the temperature in the vessel rises less than 60° C.

5. The method according to claim 1, wherein the proportion of isocyanate group-reactive component in the mixture is 0.1 to 10 weight %.

6. The method according to claim 1, wherein the mixing device comprises one or more static mixers.

7. The method according to claim 1, wherein after the end of the batch production the mixing device remains in the flooded state at ambient temperature until the start of the next batch production.

8. A method comprising introducing a reacting mixture into a storage or transport vessel, wherein the reacting mixture comprising an isocyanate group containing prepolymer from an isocyanate group-containing component and an isocyanate group-reactive component is prepared according to the method of claim 1.

* * * * *